United States Patent [19]
Fontenot et al.

[11] Patent Number: 5,081,146
[45] Date of Patent: Jan. 14, 1992

[54] METHOD AND FEED SUPPLEMENT FOR THE FEEDING OF RUMINANTS

[75] Inventors: Joseph P. Fontenot, Blacksburg, Va.; Michel Huchette, Merville, France

[73] Assignee: Roquette Freres, Lestrem, France

[21] Appl. No.: 424,098

[22] Filed: Oct. 20, 1989

[51] Int. Cl.⁵ ............................................. A61K 31/35
[52] U.S. Cl. ................................................... 514/460
[58] Field of Search ........................................ 514/460

[56] References Cited

FOREIGN PATENT DOCUMENTS 0139595 5/1985 European Pat. Off. .

OTHER PUBLICATIONS

Chemical Abstracts, vol. 104, (1986), 108401m.

Primary Examiner—Frederick E. Waddell
Assistant Examiner—Kevin Weddington
Attorney, Agent, or Firm—Fleit, Jacobson, Cohn, Price, Holman & Stern

[57] ABSTRACT

A method for feeding ruminants being fattened for meat production, a feed supplement and a complete feed for ruminants. In the method for feeding ruminants, the ruminants are fed sorbitol and at least one ionophore antibiotic in addition to their normal feedstuff. The feed supplement contains sorbitol and at least one ionophore antibiotic together with a carrier. The complete feed contains sorbitol and at least one ionophore antibiotic in addition to a normal feedstuff for ruminants. Feeding of sorbitol and at least one ionophore antibiotic to ruminants in addition to their normal feedstuff significantly improves feed efficiency.

9 Claims, No Drawings

METHOD AND FEED SUPPLEMENT FOR THE FEEDING OF RUMINANTS

FIELD OF THE INVENTION

The present invention relates to a method for a feeding of ruminants, i.e., bulls, heifers, steers and sheep, which are fattened for the purpose of meat production. The invention further relates to a feed supplement which is useful in the inventive method of feeding ruminants and to feedstuffs which are supplemented with the inventive feed supplement.

BACKGROUND OF THE INVENTION

A known means for evaluating the efficiency of a feed for fattening ruminants is the so-called "feed efficiency". The feed efficiency is the ratio of the quantity of ingested feedstuff to the gain in live weight of the animal being fattened. A decrease in the quantity of feed per unit of gain in live weight of the animal represents an improvement of the feed efficiency. In order to minimize the amount of feedstuff required to fatten an animal, livestock feeders obviously try to increase the feed efficiency of the feedstuff Further, for economic reasons, livestock feeders try to reduce as much as possible the amount of ingested feedstuff per unit of gain in live weight. Livestock feeders are particularly concerned with increasing the feed efficiency of feedstuffs in connection with the fattening of ruminants for the production of meat, since only part of the ingested feedstuff is used by the ruminants for growing.

In this connection, it has previously been proposed to protect at least certain constituents of the feedstuff in order to avoid degradation inside the rumen and in order to permit these constituents of the feedstuff to reach the duodenum of the animal. For example, it has been proposed to protect certain constituents of the feedstuff by tanning or by encapsulation.

In addition, in order to improve the feed efficiency, it has been proposed to use ionophore antibiotics, especially monensin, or lasalocid. These ionophore antibiotics act at the level of the rumen by modification of the fermentations therein. The consequence of these ionophore antibiotics is increased production of propionic acid, which propionic acid is the principle source of endogenous glucose, and decreased production of acetic and butyric acid. However, although ionophore antibiotics provide a degree of improved feed efficiency, it is desirable to further increase feed efficiency since the profit margin in feeding ruminants is usually very narrow.

It has also been proposed to introduce probiotic microorganisms or isoacids into the feedstuff. However, the results of the use of probiotic germs or isoacids have not provided a sufficient systematically beneficial effect.

Finally, a method of optimizing the assimilation of the feed ration in fattening ruminants is described in UK Patent Application GB 2,159,690. This patent application proposes providing ruminants with an effective amount of sorbitol in addition to their normal feed ration, and suggests that the gain in weight is increased without a correspondingly larger consumption of feedstuff.

The present Applicants have now discovered that the feed efficiency is surprisingly and substantially increased when ruminants to be fattened ingest an effective amount of both sorbitol and at least one ionophore antibiotic in addition to their normal feedstuff.

Therefore, it is an object of the present invention to provide a method of feeding ruminants which achieves a higher feed efficiency than prior feeding methods.

It is a further object of the present invention to provide a feed supplement which effectively increases the feed efficiency of feeding ruminants.

It is another object of the present invention to provide a feedstuff for ruminants which includes a feed supplement for improving the feed efficiency of feeding ruminants.

Additional objects and advantages of the present invention will be apparent from the following detailed description of the invention and the examples thereof which follow.

SUMMARY OF THE INVENTION

According to one aspect of the present invention, there is provided a method for feeding ruminants which comprises providing the ruminants with feedstuff, sorbitol and at least one ionophore antibiotic. Preferably, the ruminants are provided with the feedstuff ad libitum, i.e. the ruminants are provided with unrestricted access to the feedstuff.

The invention further relates to a feed supplement comprising sorbitol and at least one ionophore antibiotic together with suitable carriers. The inventive feed supplement is a mixture in solid form or can be provided as an aqueous dispersion.

In accordance with the present invention, the sorbitol and the ionophore antibiotic can be added directly to a complete feed for ruminants. Accordingly, the present invention also relates to a complete feed intended for ruminants to be fattened for meat production. The complete feed of the present invention comprises a normal feedstuff typically used in feeding ruminants being fattened for meat production, and additionally contains sorbitol and at least one ionophore antibiotic.

DETAILED DESCRIPTION OF THE INVENTION

The method of feeding ruminants in accordance with the present invention comprises providing the ruminants with feedstuff, sorbitol and at least one ionophore antibiotic. Preferably, the ruminants are provided with the feedstuff ad libitum.

According to one embodiment of the present invention, the ruminants are fed at least 10 g per day and at most 250 g per day of sorbitol and at least 0.05 mg per kg living ruminant weight and at most 2.5 mg per kg of living ruminant weight per day of at least one ionophore antibiotic.

According to an alternative embodiment of the inventive method, the sorbitol is fed to the ruminants during selected periods of about 5 days per month, with the ionophore antibiotic being fed daily. In this embodiment, the sorbitol is fed to the ruminants either for about 5 consecutive days or on 5 separate days, approximately every 6th day.

In either of the above methods, that is, in the method of feeding ruminants which comprises feeding the ruminants sorbitol and at least one ionophore antibiotic daily or the method of feeding ruminants at least one ionophore antibiotic daily and feeding sorbitol during a period of about 5 days per month, the feeding of the sorbitol and the ionophore antibiotic can be simultaneous with the feeding of the normal feedstuff.

The ionophore antibiotics which are particularly useful in the present invention are monensin and lasalocid, with monensin being especially preferred.

According to a particularly advantageous embodiment of the inventive method, the ruminants are provided with an amount of at least 20 g per day and at most 100 g per day of sorbitol. An amount of about 50 g per day is particularly preferred.

Preferably, the amount of the ionophore antibiotic, particularly monensin, provided to the ruminants is at least 0.1 mg per kg of living ruminant weight per day and at most 1.5 mg per kg of living ruminant weight per day.

The sorbitol useful in the present invention may be in the form of a powder or a solution. The sorbitol may be pure sorbitol; however, the sorbitol may also be provided in the form of a hydrogenated starch hydrolysate, of which sorbitol constitutes the principal component and represents, preferably, at least 70% by weight with respect to the dry matter of the hydrolysate.

The feed supplement of the present invention comprises sorbitol and at least one ionophore antibiotic, preferably monensin, together with suitable carriers. The respective proportions of sorbitol and the ionophore antibiotic with respect to feed dry matter in the feed supplement is from 5% to 90% by weight sorbitol and from about 70 ppm to about 0.2% by weight ionophore antibiotic. The feed supplement is a mixture in solid form or an aqueous dispersion.

In addition, sorbitol and the ionophore antibiotic can be added directly to a complete feed comprising a normal feedstuff for ruminants being fattened for meat production. The complete feed in accordance with the present invention comprises normal feedstuff, sorbitol and at least one ionophore antibiotic. A complete feed in accordance with the present invention preferably comprises from 0.1% to 5% of sorbitol of the total ration based on the dry matter weight of the complete feed, and from 5 ppm to 150 ppm of the ionophore antibiotic.

The present invention provides a method for feeding ruminants which exhibits an unexpectedly and significantly improved feed efficiency as compared to other methods of feeding ruminants. The use of sorbitol and at least one ionophore antibiotic, in accordance with the present invention for feeding ruminants significantly increases the feed efficiency due to the synergistic effect produced by the use of both sorbitol and at least one ionophore antibiotic. The following examples demonstrate that, when ruminants are fed in accordance with the present invention, the feed efficiency is surprisingly and significantly increased.

EXAMPLE 1

In this example, a total of 96 young steers were divided into four groups of 24 steers each. Each group was fed a balanced ration consisting of a full-feed of corn silage, corn grain at approximately 1% of body weight and a protein supplement of soybean meal. The balanced ration was provided to the steers as a feedstuff ad libitum. Vitamin A was added to the protein supplement to provide 24,000 IU per day. All of the steers were administered the anabolic agent zeranol. Block iodized salt was provided throughout the test period.

Group 1, the control group, was fed the balanced ration ad libitum. Group 2 was fed the balanced ration ad libitum with 35 g per day of sorbitol. Group 3 was fed the balanced ration ad libitum with 350 mg per day of monensin. Group 4 was fed according to the present invention and was fed the balanced ration ad libitum with 35 g per day of sorbitol and 350 mg per day of monensin The feed consumption of each group was measured daily. Each animal was individually weighed at regular intervals of about 28 to 35 days.

Table I below shows the initial and final average weights of the four test groups and the cumulative feed efficiency as determined on the indicated days of the test period. For each group, the feed efficiency for a given period was determined by dividing the average feed intake per day by the average daily gain in live weight.

TABLE I

|  | Group 1 | Group 2 | Group 3 | Group 4 |
|---|---|---|---|---|
| Initial weight, average (kg) | 351 | 361 | 361 | 363 |
| Feed efficiency, cumulative for period ending: | | | | |
| Day 30 | 6.57 | 5.63 | 6.22 | 5.24 |
| Day 57 | 7.7 | 6.99 | 6.89 | 6.26 |
| Day 86 | 9.06 | 8.02 | 7.87 | 7.32 |
| Day 121 | 10.46 | 9.60 | 9.43 | 8.52 |
| Final weight, average (kg) | 485 | 498 | 506 | 511 |

The results in Table I clearly illustrate the significantly improved feed efficiency of the steers of Group 4, which were fed sorbitol and monensin according to the method of the invention. The feed efficiency of the steers of Group 4 is greater than the additive improvement in feed efficiency achieved by feeding the steers sorbitol alone (Group 2) or monensin alone (Group 3).

More specifically, Group 2 showed a feed efficiency increase of 8.2% compared to the control group, Group 1, and Group 3 showed a feed efficiency increase of 9.9% compared to Group 1. Group 4, which was fed according to the invention, showed a feed efficiency increase of 8.5%.

EXAMPLE 2

The test procedure of Example 1 was followed, with the exception that five groups of 24 steers were tested, instead of four groups.

Groups 5 to 8 of this example were fed in the same manner as Groups 1 to 4 of Example 1, respectively. That is, Group 5 was a control group, Group 6 was fed sorbitol only, Group 7 was fed monensin only, and Group 8 was fed both sorbitol and monensin according to the invention. Group 9 was also fed according to the present invention. Group 9 was fed in the same manner as Group 8, with the exception that Group 9 was fed 60 g per day of sorbitol, instead of 35 g per day.

The feed intake, weight and feed efficiency were determined as in Example 1. The results are set forth in Table II below.

TABLE II

|  | Group 5 | Group 6 | Group 7 | Group 8 | Group 9 |
|---|---|---|---|---|---|
| Initial weight, average (kg) | 310 | 309 | 310 | 310 | 308 |
| Feed efficiency, cumulative for the period ending on: | | | | | |
| Day 29 | 4.44 | 3.95 | 3.72 | 3.79 | 3.51 |
| Day 57 | 5.68 | 5.38 | 4.93 | 4.84 | 4.73 |

TABLE II-continued

|  | Group 5 | Group 6 | Group 7 | Group 8 | Group 9 |
|---|---|---|---|---|---|
| Day 85 | 6.63 | 6.37 | 6.15 | 5.96 | 5.74 |
| Day 113 | 7.39 | 7.17 | 7.12 | 6.76 | 6.43 |
| Day 142 | 7.63 | 7.50 | 7.39 | 7.09 | 6.73 |
| Day 169 | 7.87 | 7.73 | 7.60 | 7.25 | 7.04 |
| Final weight, average (kg) | 511 | 503 | 502 | 506 | 498 |

The results in Table II illustrate the improved feed efficiency of the steers of Groups 8 and 9, which were fed sorbitol and monensin in accordance with this invention. The feed efficiency of both Groups 8 and 9 is greater than the additive improvement in feed efficiency achieved by feeding steers sorbitol alone (Group 6) or monensin alone (Group 7).

More particularly, Group 6, the group fed sorbitol alone, showed a feed efficiency increase of 1.8% compared to the control group, Group 5. Group 7, which was fed monensin alone, showed a feed efficiency increase of 3.4% compared to Group 5. Groups 8 and 9, which were fed both sorbitol and monensin according to the invention, showed feed efficiency increases of 7.9% and 10.5%, respectively.

Particularly large increases in feed efficiency by feeding steers in accordance with this invention were achieved in Group 9 during the first 113 days of the test. On day 113, the increases in cumulative feed efficiency for comparative Groups 6 and 7 were 3.0% and 3.7%, respectively. In contrast, Group 9, which was fed according to the present invention, showed an increase in feed efficiency of 13%.

Although the invention has been described by reference to specific embodiments and examples thereof, it is to be understood that modifications can be made without departing from the scope of the present invention as described above and as defined in the claims which follow.

What is claimed is:

1. A method for feeding ruminants which are being fattened for meat production, said method comprising providing said ruminants over a period of time with a feedstuff, sorbitol in an amount sufficient to provide a daily average of about 20 g to about 100 g, and about 0.10 mg per kg of ruminant weight to about 1.5 mg per kg of ruminant weight per day of monensin.

2. The method according to claim 1, wherein said ruminants are provided with said feedstuff ad libitum.

3. The method according to claim 1, wherein the sorbitol and the monensin are provided to said ruminants daily.

4. The method according to claim 3, wherein said ruminants are provided with said feedstuff ad libitum.

5. The method according to claim 1, wherein the sorbitol and the monensin are fed to said ruminants simultaneously with the feeding of said feedstuff.

6. The method according to claim 1, wherein the monensin is provided to said ruminants daily and the sorbitol is provided to said ruminants for a period of about 5 days per month.

7. The method according to claim 6, wherein said ruminants are provided with said feedstuff ad libitum.

8. A feed supplement for feeding ruminants which are being fattened for meat production, said feed supplement comprising a carrier containing dry matter, sorbitol and monensin, said feed supplement comprising sorbitol in an amount of about 5% to about 90% by weight based on the weight of said dry matter, and said feed supplement comprising monensin in an amount of from about 70 ppm to about 0.2% by weight, based on the weight of said dry matter.

9. A complete feed for feeding ruminants which are being fattened for meat production, said complete feed comprising a feedstuff, sorbitol and at least one monensin, said complete feed comprising about 0.1% to about 5.0% by weight sorbitol, based on the total weight of the complete feed, and comprising about 5 ppm to about 150 ppm of said monensin.

* * * * *